(12) United States Patent
Manchem et al.

(10) Patent No.: US 6,528,037 B2
(45) Date of Patent: Mar. 4, 2003

(54) METHOD FOR DETERMINING WHETHER A COMPOUND IS AN INSULIN RECEPTOR KINASE ACTIVATOR

(75) Inventors: Prasad V. V. S. V. Manchem, South San Francisco, CA (US); Robert T. Lum, Palo Alto, CA (US); Steven R. Schow, Redwood Shores, CA (US)

(73) Assignee: Telik, Inc., South San Francisco, CA (US)

( * ) Notice: Subject to any disclaimer, the term of this patent is extended or adjusted under 35 U.S.C. 154(b) by 0 days.

(21) Appl. No.: 10/115,595

(22) Filed: Apr. 2, 2002

(65) Prior Publication Data

US 2002/0151542 A1 Oct. 17, 2002

Related U.S. Application Data

(63) Continuation-in-part of application No. 09/977,059, filed on Oct. 11, 2001.
(60) Provisional application No. 60/239,636, filed on Oct. 11, 2000.

(51) Int. Cl.$^7$ .................. A61K 49/00; A61K 31/70; A61K 31/495; A61K 31/47; A61K 31/425
(52) U.S. Cl. .................. 424/9.1; 514/25; 514/252; 514/307; 514/365; 514/471
(58) Field of Search .................. 424/9.1; 514/252, 514/471, 307, 365, 25

(56) References Cited

U.S. PATENT DOCUMENTS

| | | | |
|---|---|---|---|
| 5,830,918 A | 11/1998 | Sportsman et al. | 514/648 |
| 5,851,988 A | 12/1998 | Sportsman et al. | 514/4 |
| 6,020,374 A | 2/2000 | Geier et al. | 514/553 |
| 6,051,597 A | 4/2000 | Zhang et al. | 514/414 |

FOREIGN PATENT DOCUMENTS

| | | |
|---|---|---|
| WO | 91/03226 | 3/1991 |
| WO | 99/51225 | 10/1999 |
| WO | 00/71506 | 11/2000 |
| WO | 01/12591 | 2/2001 |

OTHER PUBLICATIONS

Carr et al., "Pathogenesis of HIV–1–protease inhibitor–associated peripheral lipodystrophy, hyperlipidaemia, and insulin resistance", *Lancet*, 352, 1881–1883 (1988).

Carr et al., "A syndrome of peripheral lipodystrophy, hyperlipidaemia and insulin resistance In patients receiving HIV protease inhibitors", *AIDS*, 12, F51–F58 (1988).

Roth et al., "Development of Cervical Fat Pads Following Therapy With Human Immunodeficiency Virus Type 1 Protease Inhibitors", *Clin. J. Infect. Dis.*, 27, 65–67 (1998).

Safrin et al., "Fat distribution and metabolic changes In patients with HIV infection", *AIDS*, 13, 2493–2505 (1999).

Carr et al., "Diagnosis, prediction, and natural course of HIV–1 protease–inhibitor–associated lipodystrophy, hyperlipidaemia, and diabetes mellitus: a cohort study", *Lancet*, 353, 2093–2099 (1999).

Behrens et al., "Impaired glucose tolerance, beta cell function and lipid metabolism in HIV patients under treatment with protease inhibitors", *AIDS*, 13, F63–F70 (1999).

Reaven, "Role of insulin resistance in human disease (Syndrome X): an expanded definition", *Annu. Rev. Med.*, 44, 121–131 (1993).

Murata et al., "The mechanism of insulin resistance caused by HIV protease inhibitor therapy", *J. Biol. Chem.*, 27, 20251–20254 (2000).

Yarasheski et al., "Insulin resistance in HIV protease inhibitor–associated diabetes", *J. Acquir. Immune. Defic. Syndr.*, 21, 209–216 (1999).

Horn, "Postcard from Athens: Insulin resistance and more at the 3rd international workshop on lipodystrophy and adverse drug events in HIV", *The PRN Notebook*™, 6(4), 28–31 (2001), available on–line at www.prn.org.

*Primary Examiner*—Russell Travers
*Assistant Examiner*—Mojdeh Bahar
(74) *Attorney, Agent, or Firm*—Heller Ehrman White & McAuliffe LLP

(57) ABSTRACT

A method for determining whether a compound is an insulin receptor kinase activator.

6 Claims, 2 Drawing Sheets

$* p < 0.05$, $** p < 0.001$ ANOVA

* $p<0.05$, ** $p<0.01$
(One-way ANOVA)

METHOD FOR DETERMINING WHETHER A COMPOUND IS AN INSULIN RECEPTOR KINASE ACTIVATOR

CROSS-REFERENCE TO RELATED APPLICATIONS

This application is a continuation-in-part of U.S. application Ser. No. 09/977,059, filed Oct. 11, 2001, which claims the priority of U.S. Provisional Application No. 60/239,636, filed Oct. 11, 2000. Both of these documents are incorporated into this application by reference.

BACKGROUND OF THE INVENTION

1. Field of the Invention

The present invention relates to a method for determining whether a compound is an insulin receptor kinase activator.

2. Description of Related Art

The insulin receptor is present on virtually all cells and at high concentrations on the cells of the liver, skeletal muscles, and adipose tissue. Stimulation of the insulin receptor with insulin is an essential element in carbohydrate metabolism and storage.

Diabetic subjects either lack sufficient endogenous secretion of the insulin hormone (Type 1) or have an impaired insulin signaling to the glucose transport system and to glycogen synthase (Type 2). In Type 2 diabetics, major insulin-responsive tissues such as liver, skeletal muscle and adipose tissue exhibit the insulin resistance (Haring and Mehnert (1993), *Diabetologia* 36: 176–182; Haring et al. (1994), *Diabetologia,* 37 Suppl. 2: S149–S154).

Insulin receptor kinase activators stimulate autophosphorylation of the insulin receptor and stimulate the uptake of glucose into cells. Without intending to be bound by any theory, it is believed that insulin receptor kinase activators act directly on the kinase function of the receptor and do not necessarily compete with insulin for binding at the insulin-binding site, nor do they effect activation of the receptor by a mechanism similar to that exhibited by insulin.

Thus, insulin receptor kinase activators are directly able to activate the kinase to autophosphorylate, to potentiate the effects of insulin, to activate the kinase function of the receptor in phosphorylating insulin receptor substrate-1 (IRS-1) and to effect the increased uptake of glucose by adipocytes and insulin receptor-bearing cells in general and to lower blood glucose in diabetic subjects.

Additionally, insulin receptor kinase activators may be used to stimulate the kinase activity of an insulin receptor, to enhance the activation of the insulin receptor by insulin, to enhance the stimulation by insulin of cellular glucose uptake, and to stimulate the uptake of glucose in subjects who have diabetes, ketoacidosis, insulin resistance, hyperglycemia, lipodystrophy, or hypertriglyceridemia.

Insulin resistance is also found in many non-diabetic individuals, and may be an underlying etiologic factor in the development of the disease (Reaven (1988), *Diabetes,* 37: 1595–1607). For example, treatments for HIV infection have proven very effective in controlling the ravages of the terminal stage of the infection, AIDS, however, many of the drugs currently available have side-effects which induce insulin resistance.

Drugs currently used to suppress viral load and the resulting AIDS symptoms are called HIV protease inhibitors. Unfortunately, HIV protease inhibitors, which are required to maintain health in HIV-infected individuals, also carry the significant side-effect of inhibitor-induced insulin resistance leading to hyperglycemia that can progress to diabetes and ultimately life threatening ketoacidosis. (Carr et al. (1998), *Lancet* 351: 1881–1883; Carr et al. (1998), *AIDS* 12: F51–F58).

In addition to insulin resistance, other related disturbances in metabolism, such as lipodystrophy and hypertriglyceridemia, are also observed in HIV protease inhibitor treated patients (Roth et al. (1998), *Clin Infect Dis* 27: 65–67; Safrin et al. (1999), *AIDS* 13: 2493–2505; Carr et al. (1999), *Lancet* 353: 2093–2099; Behrens et al. (1999), *AIDS* 13: F63–F70). This complex metabolic side-effect profile of these very important drugs has all the hallmark features of the insulin-resistant state referred to as Syndrome-X (Reaven (1993), *Annu Rev Med* 44: 121–131).

For some patients, these metabolic side-effects greatly limit the use of these life-sustaining drugs. This side-effect profile was not recognized early in the development of these drugs, but once these inhibitors entered general clinical use, this problematic side-effect manifested itself in a large percentage of the treated population. The problem appears to be a class effect in that all the currently available HIV protease inhibitor drugs demonstrate this severe effect.

The molecular origin of this phenomena was recently identified in 3T3 L1 adipocytes (Murata et al. (2000), *J Biol Chem* 275(27): 20251–20254). The report provided evidence that at least three of the commercialized HIV protease inhibitor drugs also inhibit the glucose transporter from localizing to the cell membrane with the subsequent inhibition of glucose uptake by these cells. This inhibition of cellular glucose transport into cells by these HIV protease inhibitors is consistent with the elevation of glucose and lipids observed in the clinic for some patients being treated with these protease inhibitor drugs.

In the parent application, applicants disclosed that insulin receptor kinase activators reverse the HIV protease inhibitor side effect of metabolic disorders and can reverse the effects of insulin resistance the glucose uptake inhibition so caused. Such compounds are useful in treating HIV protease inhibitor induced insulin resistance, hyperglycemia, diabetes, ketoacidosis, lipodystrophy, and hypertriglyceridemia.

The disclosures of all documents referred to in this application are incorporated herein by reference.

SUMMARY OF THE INVENTION

This invention is a method of determining whether a compound is an insulin receptor kinase activator, comprising: administering the compound to a non-human mammal concurrently treated with an HIV protease inhibitor, administering glucose to the mammal, and measuring the level of plasma insulin or plasma glucose in the mammal, where a reduced level of plasma insulin or plasma glucose in the mammal compared to a comparable mammal that has been treated with the HIV protease inhibitor and administered the glucose, but not administered the compound, indicates that the compound is an insulin receptor kinase activator.

In a preferred embodiment, the HIV protease inhibitor is amprenavir, atazanavir, droxinavir, indinavir, lopinavir, nelfinavir, ritonavir, or saquinavir, or a pharmaceutically acceptable salt thereof; especially indinavir as the sulfate salt.

In a preferred embodiment, the mammal is a rat.

DETAILED DESCRIPTION OF THE INVENTION

Figure 1:
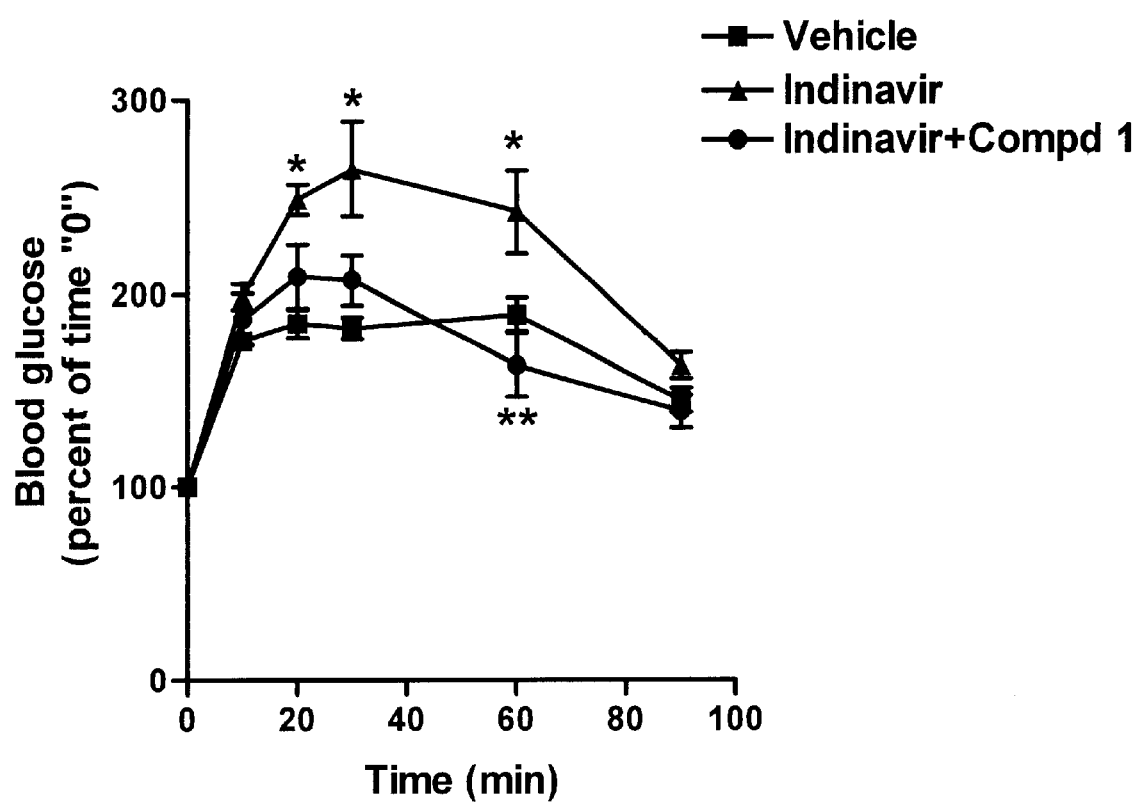
FIG. 1 shows the effect of indinavir and indinavir plus an insulin receptor kinase activator on blood glucose levels in rats following oral glucose challenge.

The method of the present invention is used to determine whether a compound is an insulin receptor kinase activator. It comprises administering a compound to a non-human mammal concurrently treated with an HIV protease inhibitor, administering glucose to the mammal, and measuring the increase in plasma insulin or plasma glucose in the mammal, wherein a reduced increase in plasma insulin or plasma glucose in the mammal compared to a comparable mammal that has been treated with the HIV protease inhibitor and administered the glucose, but not administered the compound, indicates that the compound is an insulin receptor kinase activator.

Concurrent treatment means that the compound is administered at the same time the HIV protease inhibitor is administered or, at least, that the compound is administered at some time when the glucose metabolism of the animal is impaired by the action of the HIV protease inhibitor.

The insulin receptor kinase activators found by the method of this invention can be used for the uses disclosed in the section "Background to The Invention" discussed above.

The method of this invention comprises concurrent administration of the compound to be tested and an effective amount of an HIV protease inhibitor, followed or accompanied by administration of an effective amount of glucose. The preferred route of administration is oral.

An effective amount of glucose is the amount that produces a readily measurable increase in blood glucose or insulin levels shortly after administration in a normal mammal of the species being used in the method. A suitable effective amount of glucose in the rat is about 2.5 g/Kg orally.

An effective amount of the HIV protease inhibitor is the amount that produces a readily measurable difference between the blood glucose or insulin level in a mammal that has been administered the HIV protease inhibitor and glucose relative to a comparable mammal that has been administered glucose alone. A suitable effective amount for indinavir sulfate in the rat is from about 75 mg/Kg to about 100 mg/Kg orally.

A person of ordinary skill in the art will have no difficulty, having regard to that skill and this disclosure, in determining suitable amounts of glucose and HIV protease inhibitor for different mammalian species and for different HIV protease inhibitors.

The compound to be tested is desirably administered in an amount that produces a readily measurable difference between the blood glucose or insulin level in a mammal that has been administered the HIV protease inhibitor, the compound, and glucose relative to a comparable mammal that has been administered the HIV protease inhibitor and glucose alone, especially an amount that produces blood glucose or insulin levels comparable to those of a comparable mammal administered glucose alone. Comparison of the amounts of a test compound with the amount of a known insulin receptor kinase receptor activator required to give the same blood glucose or insulin levels under the same test conditions will give an indication of the potency of the compound; and in this manner the method provides not just an indication of whether a compound is an insulin receptor kinase activator, but also how potent it is.

The following examples are given to enable those skilled in the art to more clearly understand and to practice the present invention. They should not be considered as limiting the scope of the invention, but merely as being illustrative and representative thereof.

EXAMPLE 1

Preparation of Compound 1, an Insulin Receptor Kinase Activator

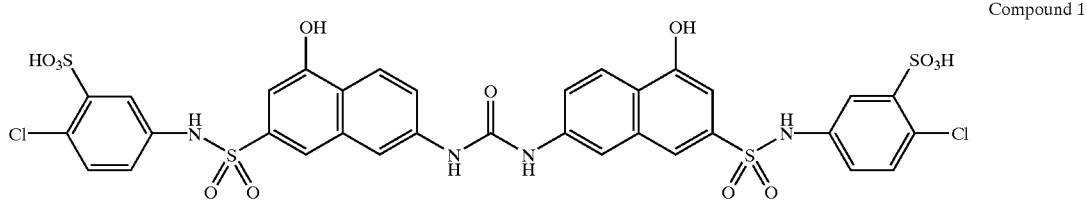

Compound 1

The preparation of Compound 1 is described in the Examples of WO 00/71506, and is also provided below.

4-hydroxy-7-{[(5-hydroxy-7-sulfo(2naphthyl))amino] carbonylamino}-naphthalene-2-sulfonic acid disodium salt. To 10.77 g (0.045 moles) of 7-amino-4-hydroxynaphthalene-2-sulfonic acid dissolved in 45 mL of 1 N aqueous NaOH and 50 mL of water was added 3.70 g (0.045 moles) of sodium acetate. The pH of the solution was above 9. The reaction was cooled to under 5° C. in an ice-water bath. Then, 2.23 g (0.045 mole) of triphosgene dissolved in 15 mL of THF was added in three portions. The pH of the reaction fell to 4–5 and was readjusted to 7–8 by the dropwise addition of 1 N aqueous NaOH. TLC (6:2:1 ethyl acetate:isopropanol:water) indicated the reaction was incomplete. Another 2.20 g (0.045 moles) of triphosgene in 10 mL of THF was added portionwise with the pH kept above 7 by the addition of 1 N aqueous NaOH. When the reaction was judged complete by TLC, the pH was lowered to 1 with aqueous HCl and the volatiles were removed by rotary evaporation. The solid product was collected by vacuum filtration. This resulted in the recovery of 10.85 g of the desired compound.

7-{[(7-(chlorosulfonyl)-5-hydroxy(2-naphthyl))amino] carbonylamino}-4- hydroxy-naphthalene-2-sulfonyl chloride. To 500 mg (0.912 mmol) of 4-hydroxy-7-{[(5-hydroxy-7-sulfo-(2-naphthyl))amino] carbonylamino}naphthalene-2-sulfonic acid disodium salt suspended in 8 mL of phosphorus oxychloride was added 25 mL. of 1:1 (v:v) sulfolane:acetonitrile and 0.5 mL of dimethylacetamide. The reaction mixture was allowed to stir at ambient temperature for 16 hours. The reaction became a clear solution which was poured onto 500 mL of ice. The ice mixture was placed in an ice bath and allowed to warm to room temperature. The resulting solid was collected by vacuum filtration and was washed with water. The solid was dried under high vacuum for 24 hours. This provided 412 mg of desired compound.

5-{[(7-{[N-(7-{[(4-chloro-3-benzenesulfonic acid)amino]sulfonyl}-5-hydroxy-(2-naphthyl)carbamoyl]amino}-4-hydroxy(2-naphthyl))sulfonyl]amino}-2-chlorobenzensulfonic acid. To 0.15 g (0.277 mmol) of 7-{[(7-(chlorosulfonyl)-5-hydroxy-(2-napthyl))amino]carbonyl-amino}-4-hydroxynaphthalene-2-sulfonyl chloride was added 1.5 mL of freshly distilled THF followed by 0.105 g (0.610 mmol) of 5-amino-2-chlorobenzenesulfonic acid. To this solution was added 67 μL (0.831 mmol) of pyridine. The reaction was allowed to stir at ambient temperature for 16 hours. Then, the reaction was partitioned between 1 N HCl (aqueous) and ethyl acetate. The aqueous layer was extracted a second time with ethyl acetate and the combined organic layers were dried (MgSO4). filtered and volatiles removed by rotary evaporation. This provided 0.14 g of the desired compound.

EXAMPLE 2

Reversal of Protease Inhibitor-Mediated Insulin Resistance in Normal Rats by Compound 1

Seven to nine week-old male CD rats (Charles River Laboratories, Hollister, Calif.) were used to study the effects of protease inhibitor and compound 1, described above. Rats were housed 3 per cage under standard conditions with a 12 hour on/off light cycle. Each cage contained heat-treated hardwood chip bedding. The rats had access to food and water and allowed a minimum of one week to acclimate before being used in the experiment.

Animals were fasted overnight before the experiment. On the day of the experiment, the animals were weighed and randomly divided into three groups.

Indinavir sulfate was prepared as a 50 mg/mL aqueous solution; Compound 1 was prepared as a 5 mg/mL solution in aqueous 45% polyethylene glycol 400; and glucose was prepared as a 250 mg/mL aqueous solution. Eight animals (average weight 300 grams) were used in each group; and the groups were treated with vehicle, 100 mg/Kg of indinavir sulfate, or 100 mg/Kg of indinavir sulfate plus 10 mg/kg of Compound 1 by oral gavage. After 30 min, all animals were challenged with 2.5 g/Kg oral glucose, and plasma glucose measurements were taken at 0 min, 10 min, 20 min, 30 min, 60 min, 90 min, and 120 min by tail bleeding. Glucose measurements were made with a Glucometer and Glucose strips (Bayer).

Blood samples were obtained via a tail incision at 0 min and 30 min time points and analyzed for plasma insulin levels by ELISA (ALPCO Diagnostics, Windham, N.H.).

Figure 2:
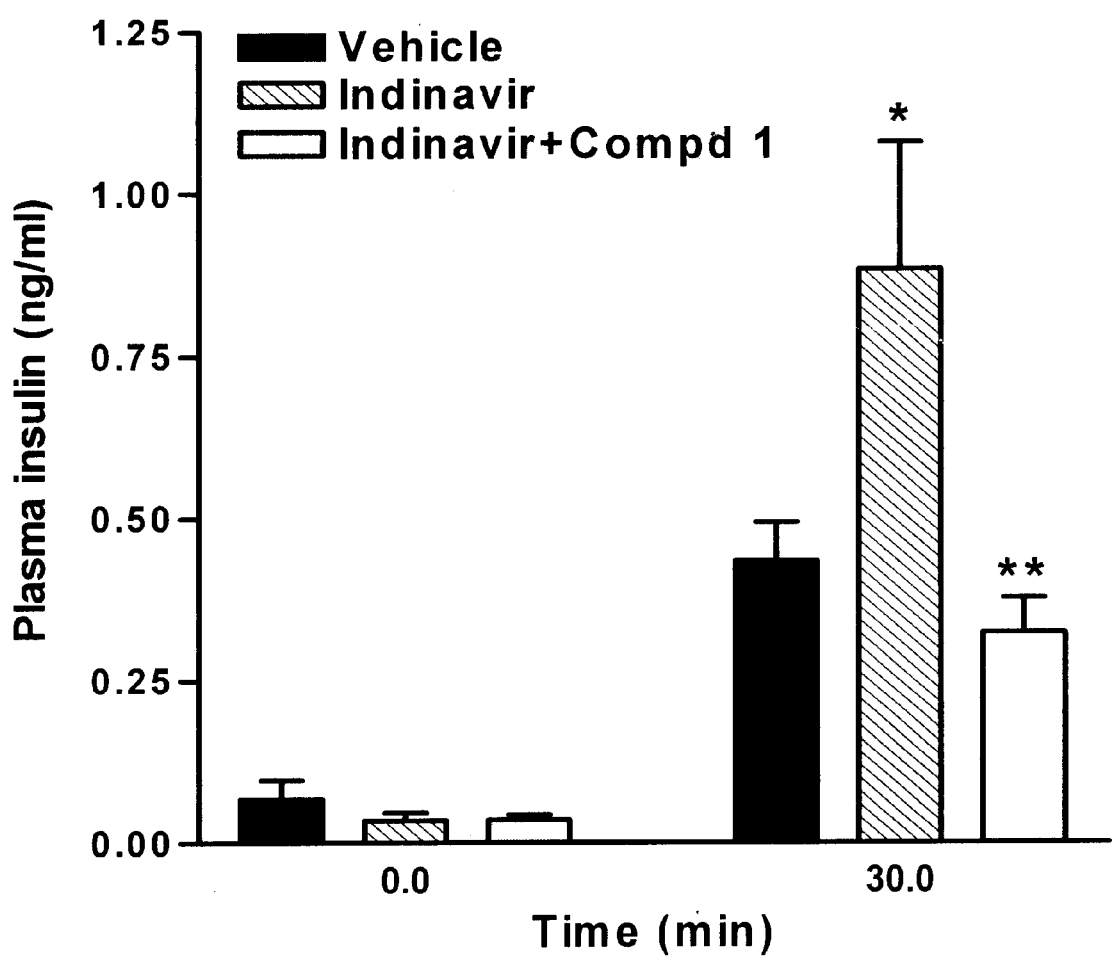
FIG. 2 shows the effect of indinavir and indinavir plus an insulin receptor kinase activator on plasma insulin levels in rats following oral glucose challenge.

The resulting data are shown in FIGS. 1 and 2. FIG. 1 shows the effect of indinavir sulfate and indinavir sulfate plus Compound 1 on plasma glucose levels following oral glucose challenge. The plasma glucose levels are reported as the percentage of the values before challenge ("zero time" values). FIG. 2 shows the effect of indinavir sulfate and indinavir sulfate plus Compound 1 on plasma insulin levels.

Both Figures show the effect of a insulin receptor kinase activator on the glucose-challenged HIV protease inhibitor-treated rat; and demonstrate how the method of this invention enables the determination of whether a compound is an insulin receptor kinase activator.

We claim:

1. A method for screening a compound to determine its activity as an insulin receptor kinase activator, comprising:

administering the compound to a non-human mammal concurrently treated with an HIV protease inhibitor;

administering glucose to the non-human mammal; and measuring the level of plasma insulin or plasma glucose in the non-human mammal, where a reduced level of plasma insulin or plasma glucose in the non-human mammal compared to a comparable non-human mammal that has been treated with the HIV protease inhibitor and administered the glucose, but not administered the compound, indicates that the compound is an insulin receptor kinase activator.

2. The method of claim 1 where the level of plasma glucose is measured.

3. The method of claim 1 where the level of plasma insulin is measured.

4. The method of claim 1 where the HIV protease inhibitor is selected from amprenavir, atazanavir, droxinavir, indinavir, lopinavir, nelfinavir, ritonavir, saquinavir, and their pharmaceutically acceptable salts.

5. The method of claim 4 where the HIV protease inhibitor is indinavir sulfate.

6. The method of claim 1 where the non-human mammal is a rat.

* * * * *